(12) United States Patent
Latham et al.

(10) Patent No.: US 9,713,676 B2
(45) Date of Patent: Jul. 25, 2017

(54) AUTOINJECTORS

(75) Inventors: David Latham, Oxfordshire (GB); Robert Wozencroft, Surrey (GB)

(73) Assignee: OWEN MUMFORD LIMITED, Oxford (GB)

(*) Notice: Subject to any disclaimer, the term of this patent is extended or adjusted under 35 U.S.C. 154(b) by 986 days.

(21) Appl. No.: 13/997,488

(22) PCT Filed: Dec. 22, 2011

(86) PCT No.: PCT/GB2011/052561
§ 371 (c)(1),
(2), (4) Date: Aug. 7, 2013

(87) PCT Pub. No.: WO2012/085584
PCT Pub. Date: Jun. 28, 2012

(65) Prior Publication Data
US 2013/0310745 A1  Nov. 21, 2013

Related U.S. Application Data

(60) Provisional application No. 61/426,004, filed on Dec. 22, 2010.

(30) Foreign Application Priority Data

Dec. 22, 2010  (GB) .................................. 1021767.7

(51) Int. Cl.
*A61M 5/20*  (2006.01)
*A61M 5/315*  (2006.01)
(Continued)

(52) U.S. Cl.
CPC ............ *A61M 5/20* (2013.01); *A61M 5/2033* (2013.01); *A61M 5/3157* (2013.01);
(Continued)

(58) Field of Classification Search
CPC .................. A61M 5/20; A61M 5/2033; A61M 2005/2418; A61M 2005/2073;
(Continued)

(56) References Cited

U.S. PATENT DOCUMENTS

2003/0083611 A1  5/2003 Angel et al.
2005/0020983 A1  1/2005 Schreijag et al.
(Continued)

FOREIGN PATENT DOCUMENTS

GB          2460398 A       2/2009
GB   WO 2009141650 A2 * 11/2009 .......... A61M 5/2033
(Continued)

OTHER PUBLICATIONS

Merriam-Webster Dictionary definition for "drum", available online Jan. 9, 2017 at https://www.merriam-webster.com/dictionary/drum.*

(Continued)

*Primary Examiner* — Kevin C Sirmons
*Assistant Examiner* — Amber Stiles
(74) *Attorney, Agent, or Firm* — Young & Thompson

(57) ABSTRACT

An autoinjector includes a body (10, 12), a syringe (13) or cartridge disposed within the body, and a plunger (60) moveable during operation between a first and a second position to effect an injection, the plunger including a transverse passage (66) containing a moveable magnetic element (68) of a magnetic pair, the body including another magnetic element (54) at a position such that, on the plunger reaching and/or nearing its second position, the magnetic attraction therebetween causes a sound-emitting impact, the plunger (60) including a magnetic keeper element (72) mounted adjacent the transverse passage and adapted to hold the movable magnetic element (68) against movement until
(Continued)

attraction by the other magnetic pair element (54), wherein the keeper element (72) is disposed on the longitudinal axis.

11 Claims, 12 Drawing Sheets

(51) Int. Cl.
    *A61M 5/32*     (2006.01)
    *A61M 5/24*     (2006.01)

(52) U.S. Cl.
    CPC ....... *A61M 5/31533* (2013.01); *A61M 5/3204* (2013.01); *A61M 5/326* (2013.01); *A61M 2005/206* (2013.01); *A61M 2005/2073* (2013.01); *A61M 2005/2418* (2013.01); *A61M 2005/3247* (2013.01); *A61M 2205/581* (2013.01); *A61M 2207/00* (2013.01)

(58) Field of Classification Search
    CPC ........ A61M 5/3157; A61M 2005/3247; A61M 5/3204; A61M 5/31533; A61M 2207/00; A61M 2005/206; A61M 2205/581; A61M 5/326
    See application file for complete search history.

(56) References Cited

U.S. PATENT DOCUMENTS

| | | | |
|---|---|---|---|
| 2005/0273059 A1* | 12/2005 | Mernoe | A61M 5/14248 604/180 |
| 2006/0173409 A1 | 8/2006 | Yang | |
| 2006/0175427 A1 | 8/2006 | Jonientz et al. | |
| 2010/0278368 A1* | 11/2010 | Martin | H04R 1/30 381/340 |

FOREIGN PATENT DOCUMENTS

| | | |
|---|---|---|
| WO | 2007132353 A2 | 11/2007 |
| WO | 2008/083875 | 7/2008 |
| WO | 2009/141650 | 11/2009 |

OTHER PUBLICATIONS

GB Search Report, dated Feb. 25, 2011, from corresponding PCT application.

International Search Report dated Jun. 29, 2012, corresponding to PCT/GB2011/052561.

* cited by examiner

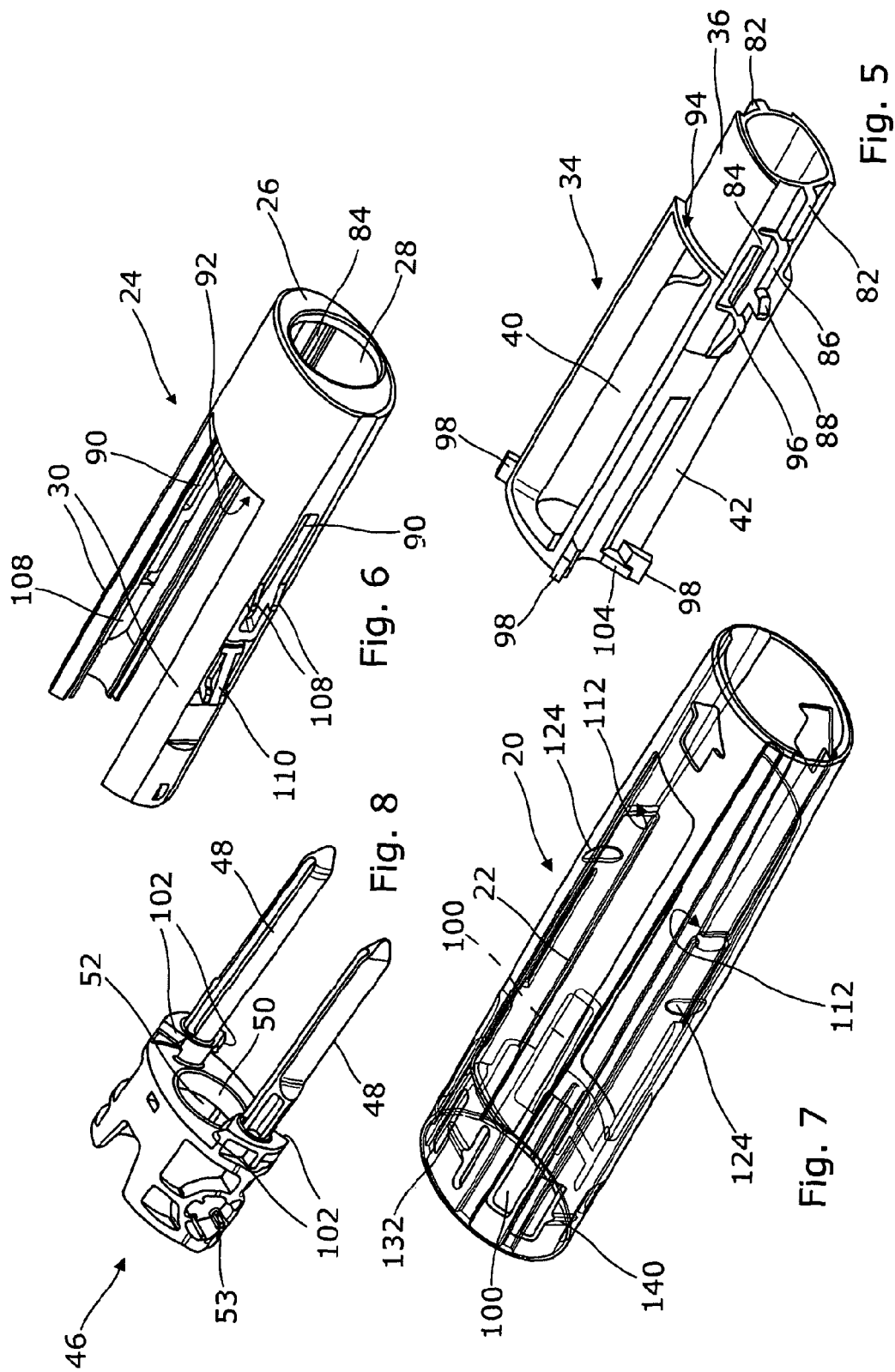

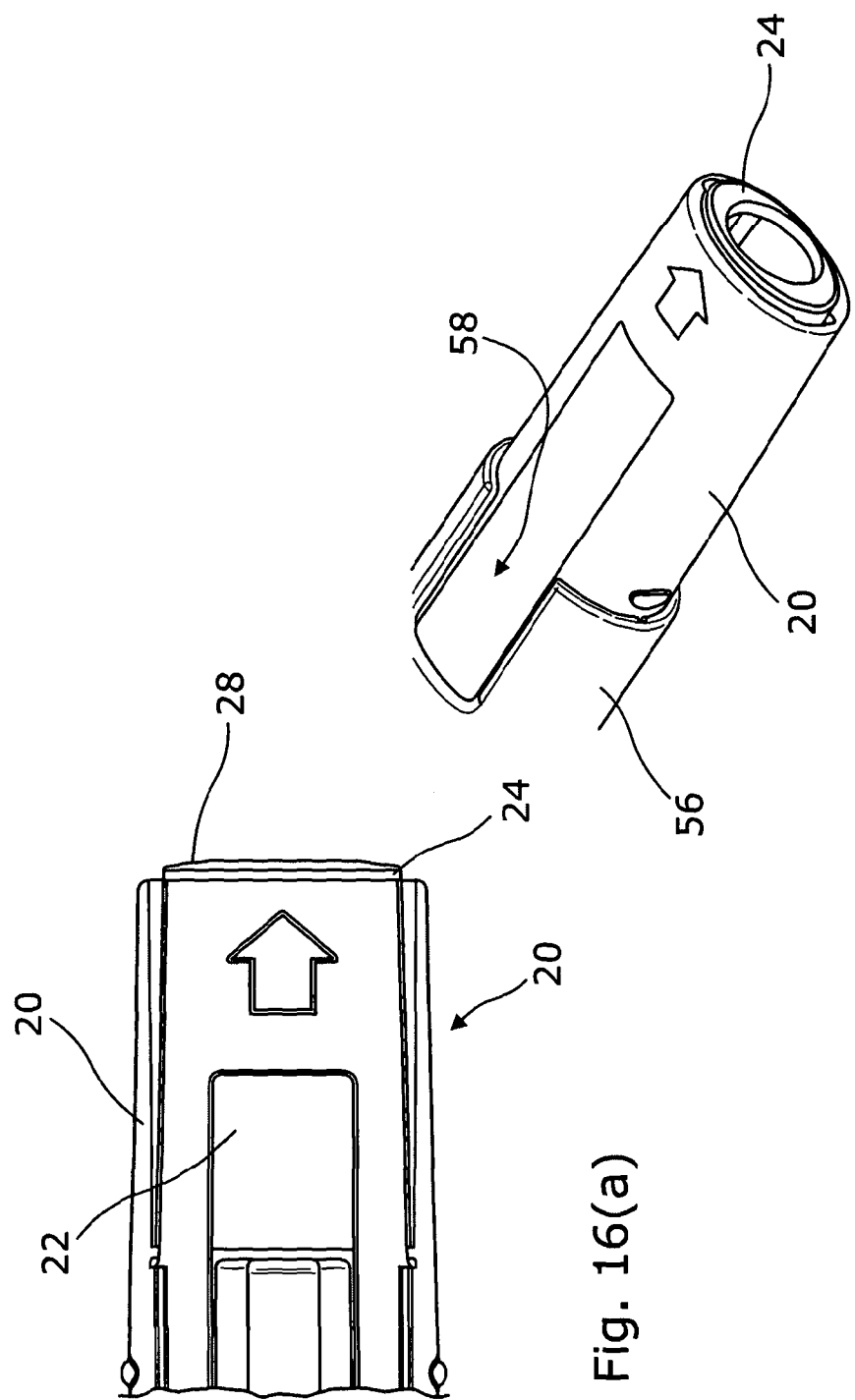

AUTOINJECTORS

This invention relates to autoinjectors.

We have previously proposed in WO2009/141650 an autoinjector in which satisfactory completion of the injection operation and delivery of the dose is signalled to the user by a magnetically-generated audible click. In this device an elongate drive plunger is provided with a transverse passage which is blind at one end. A fixed keeper is buried in the blind end of the passage remote from the longitudinal axis of the plunger. A movable magnet contained in the passage moves from that one end of the passage to the other when the plunger moves alongside a fixed magnet in the housing wall when the plunger reaches its forward position. Our further work in this field has shown that there are substantial benefits in orienting the magnet keeper on the longitudinal axis of the device. This provides improvements as the recovery range for the magnet:magnet keeper is reduced if the magnetic ball should be dislodged from its rest position, and also assembly of the device may be simplified. Moreover, we have developed various techniques for enhancing the sound emitted.

Accordingly, in one aspect, this invention provides an autoinjector comprising a body, a syringe or cartridge disposed within said body, and a plunger moveable during operation between a first and a second position to effect an injection, the plunger including a transverse passage containing a moveable magnetic element of a magnetic pair, the body including another magnetic element at a position such that, on said plunger reaching and/or nearing its second position, the magnetic attraction therebetween causes a sound-emitting impact, the plunger including a keeper element mounted adjacent said transverse passage and adapted to hold the movable magnetic element against movement until attraction by the other magnetic pair element, wherein said keeper element is disposed on said longitudinal axis.

The term 'magnetic' is used in the sense of covering elements that are already magnetised, as well as elements of non-magnetised ferro-magnetic material commonly referred to as 'keepers'. The term magnetic pair is used broadly to cover two elements which experience magnetic forces when brought near to each other. Thus the term includes two magnets as well as a keeper and a magnet. In one arrangement, the movable magnetic element comprises a ball magnet. The magnetic element associated with said body may comprise a disc magnet. The keeper element may comprise a keeper element of ferro-magnetic material, although this could be magnetised. The keeper element may take many forms, such as a ball ring, or ring element that functions to retain the movable magnet until attracted by the other magnetic element.

In another aspect, this invention provides an autoinjector comprising a body, a syringe or cartridge disposed within said body, and a magnetically operated indicator within said body for generating an acoustic signal upon completion of an injection, the autoinjector including mechanical sound enhancement means for enhancing or amplifying the acoustic signal heard by user upon completion of an injection.

Preferably said mechanical sound enhancement means comprises one or more apertures disposed in an external wall of the body. The aperture or apertures may be of horn shape to enhance the sound characteristics thereof.

Preferably said magnetically operated indicator comprises a relatively fixed magnet associated with a wall portion of said body, and a relatively movable magnetic element associated with a drive mechanism for said syringe or cartridge, said mechanical sound enhancement means comprising a modified mounting arrangement for mounting the magnet in said body or portion.

In yet another arrangement, the mechanical sound enhancement means could comprise a drum surface or the like in the wall of the body which is energised by said magnetic impact.

Whilst the invention has been described above, it extends to any inventive combination or sub-combination of novel features set out above, or in the following description or claims.

The invention may be performed in various ways and an embodiment thereof, with various modifications, will now be described by way of example only, reference being made to the accompanying drawings in which:

FIG. 5 is an enlarged view of the syringe carrier;

FIG. 6 is an enlarged view of the needle shroud;

FIG. 7 is an enlarged view of the front body housing;

FIG. 8 is an enlarged view of the spring guide;

Figure 14A:
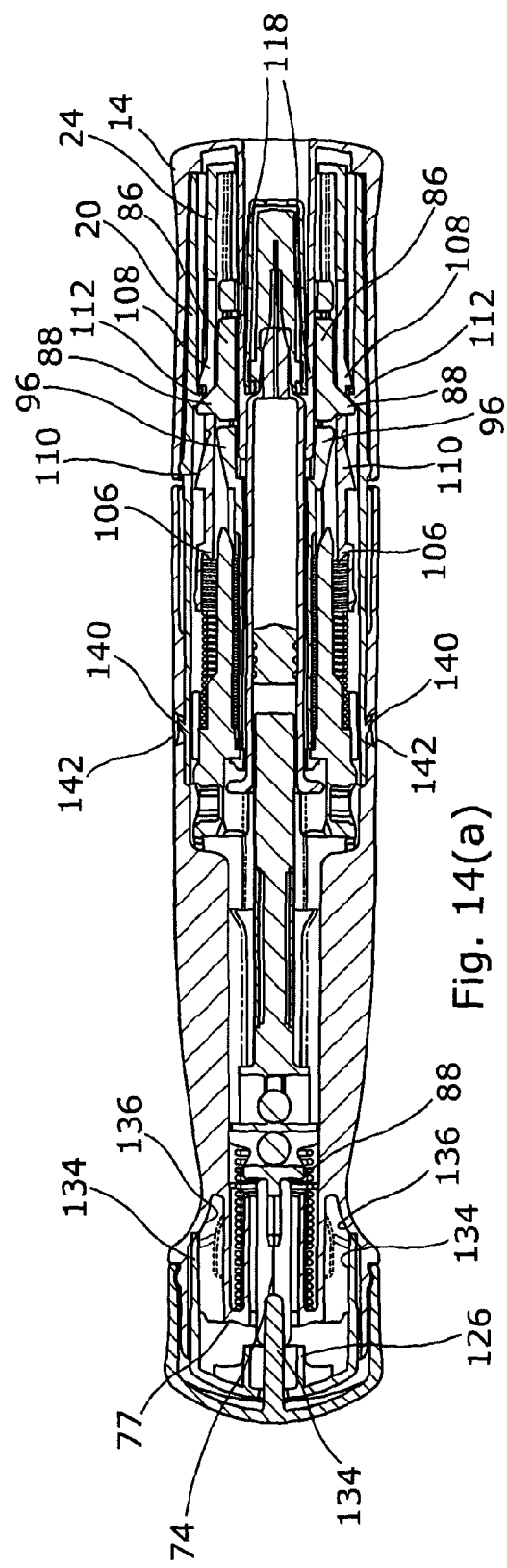
Figure 15A:
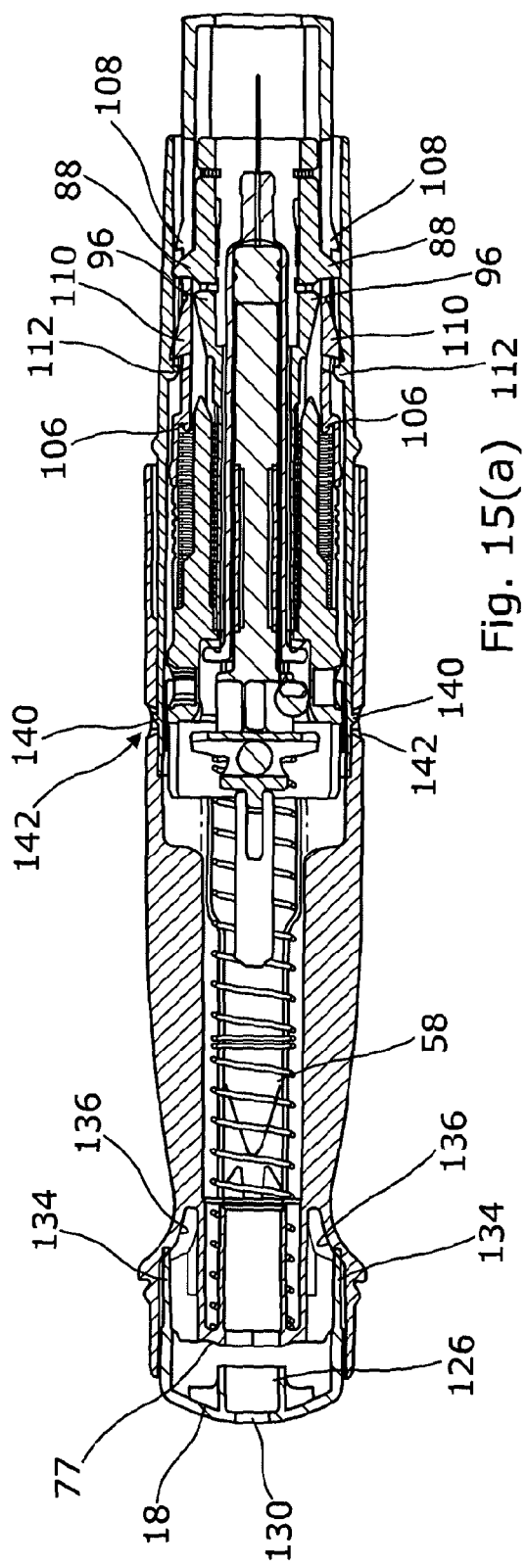

FIGS. 14(a) and (b) are transverse section views on the major and minor planes respectively of the autoinjector when in its pre-use condition;

FIGS. 15(a) and (b) are transverse section views on the major and minor planes respectively of the autoinjector after use;

FIGS. 16(a) and (b) are detail views on the front end of the device showing the forwardly dished skin-contact surface:

FIGS. 17(a) to (d) are examples of modifications designed to enhance the sound transmitted to the user when the ball magnet impacts the disc magnet, and FIGS. 18(a) and (b) are comparative views showing a keeper element in the form of a ball and a ring respectively.

Figure 1:
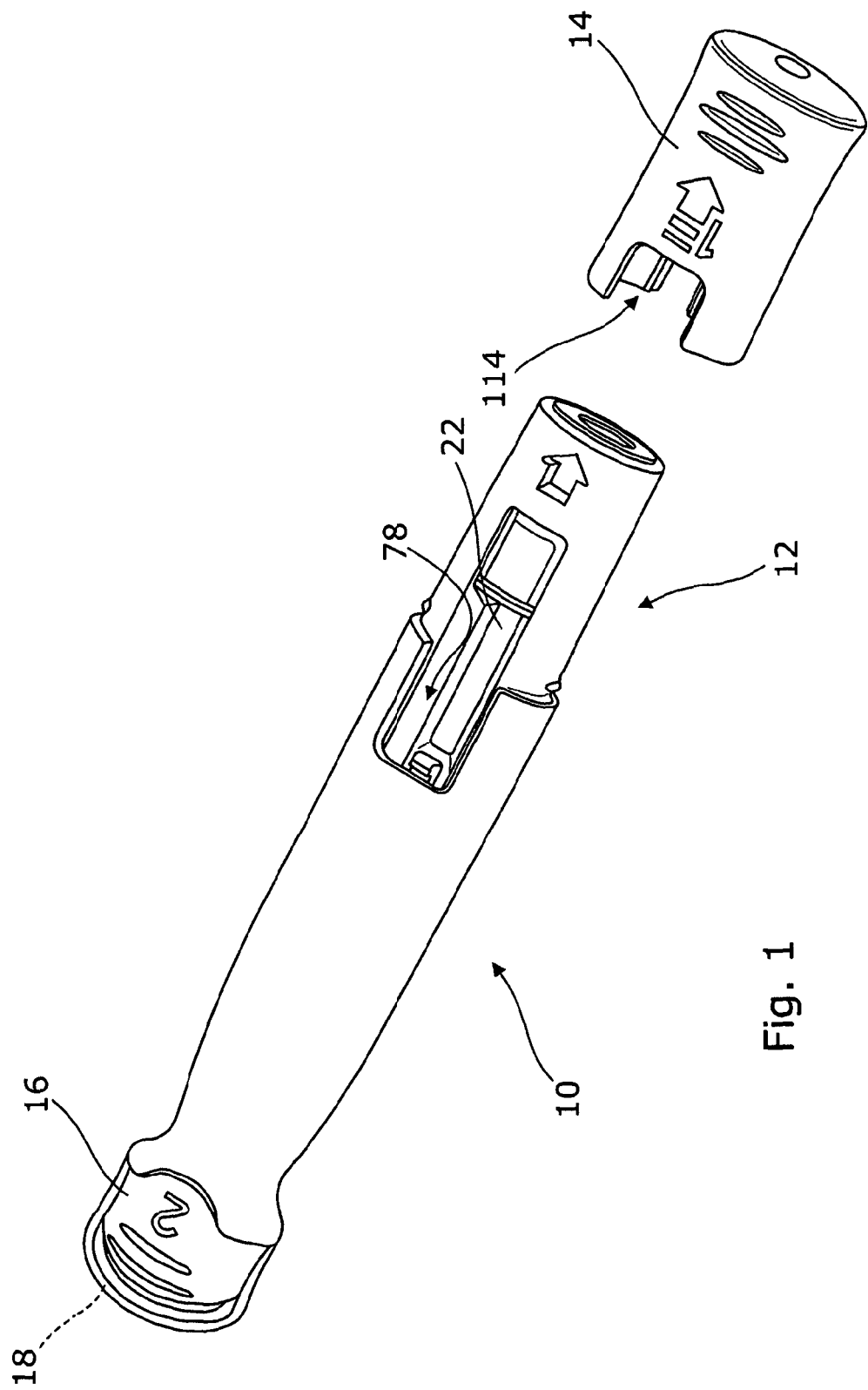
FIG. 1 is a perspective view of an autoinjector in accordance with an embodiment of this invention with the first, front cap removed prior to an injection, but before removal of the second, rear cap.
Figure 2:
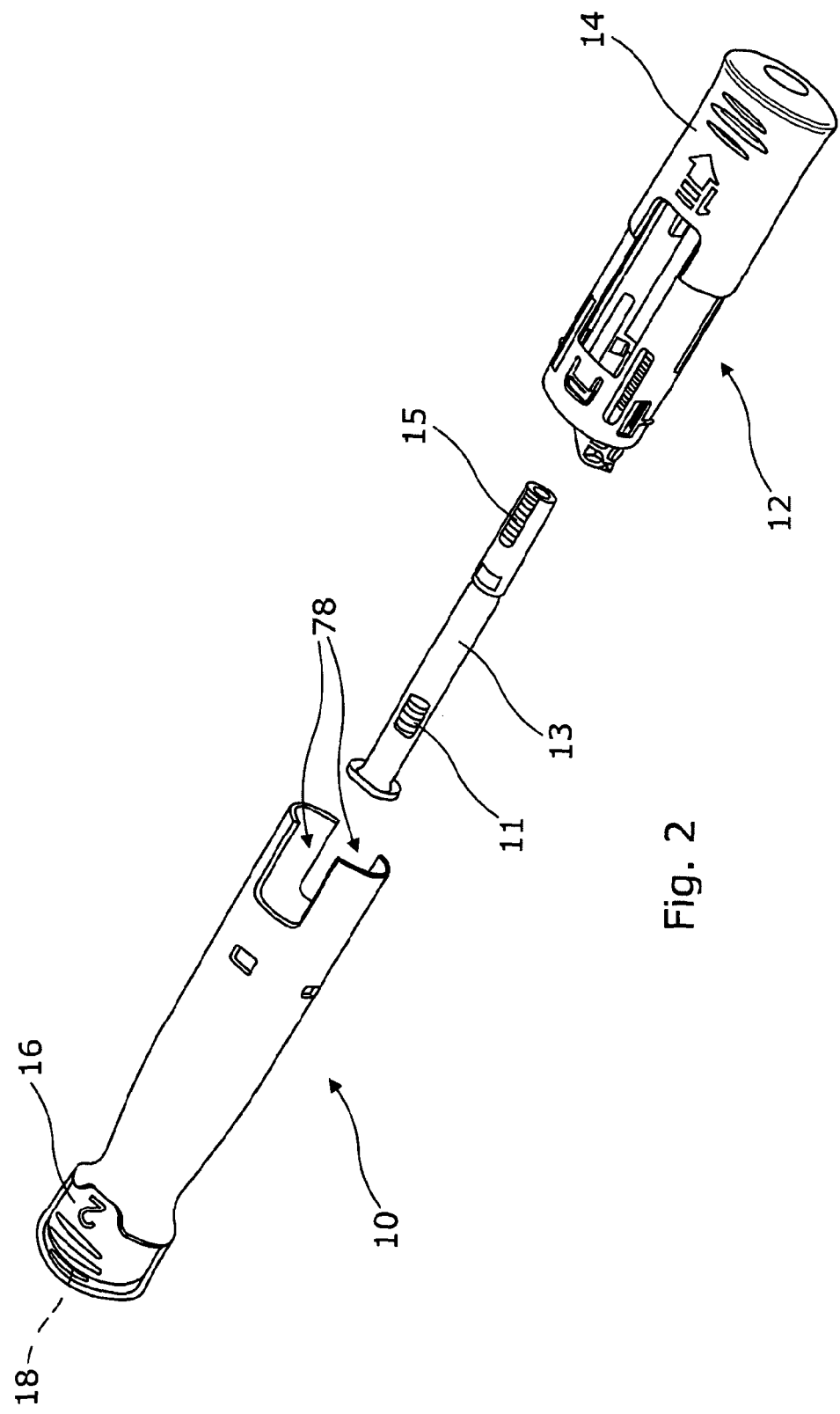
FIG. 2 is a view of the autoinjector with the rear assembly and front assembly separate prior to loading of a syringe in the forward assembly and being snap-fitted together.

The embodiment of autoinjector illustrated in the Figures and described below is designed automatically to inject a selected dose of medicament when offered up an injection site and fired. Referring initially to FIGS. 1 and 2, the autoinjector comprises a rear assembly 10 containing a drive mechanism and a front assembly 12 for receiving a syringe 13 with medicament. The front and rear assemblies are snap-fitted together during manufacture. On the front end of the device is a removable cap 14 that also serves as needle shield remover as to be described below. On the rear end of the rear assembly is a rear cap 16 which includes a safety pin which prevents premature firing of the drive mechanism, the rear cap also covering the firing button 18.

Figure 3:
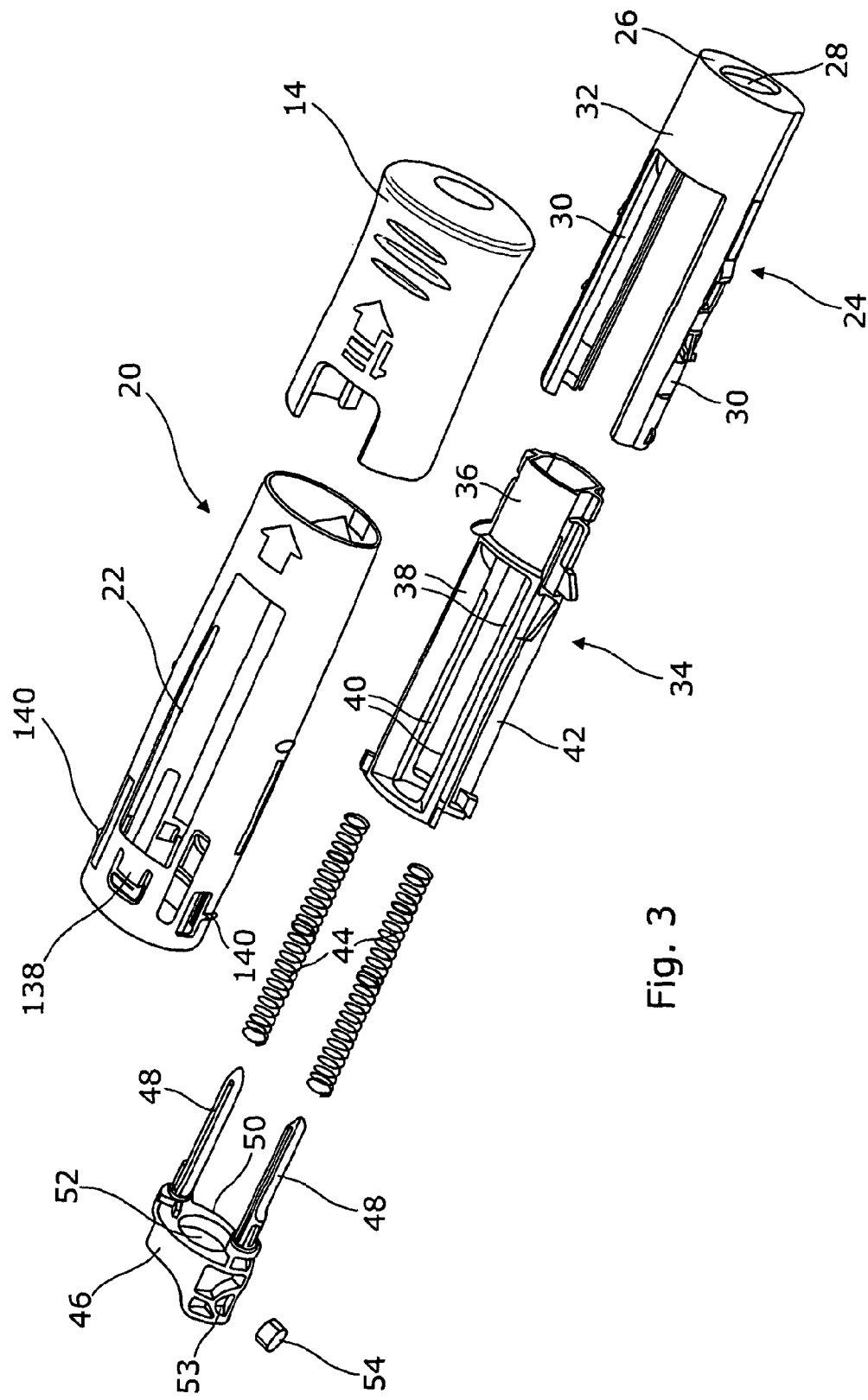
FIG. 3 is an exploded view of the front assembly.

Referring now to FIG. 3, the front assembly 12 comprises an outer body housing 20 of generally clear plastic material defining opposed integral viewing windows 22 through which the syringe can be viewed when the device has been assembled. The windows allow the whole of the dose volume of the syringe to be viewed. Apart from the clear plastic material of the windows 22, the body housing 20 may be opaque. Provision of a transparent window element, instead of the common arrangement of an open aperture or slot, has the advantage of preventing external access to the syringe. Also the provision of twin shroud springs spaced to either side of the longitudinal axis of the device means that the entire length of the dose volume is clearly visible without being obscured by any springs etc.

Slideably mounted within the housing 20 is a needle shroud 24 having a chamfered, conical and/or convexly curved domed front face 26 with a central aperture 28 therein to provide a forwardly dished configuration through which the needle of the syringe may project during the injection. The shroud 24 includes two rearwardly extending arms 30 of arcuate cross-section, extending back from a forward tubular section 32.

Slideably coupled to the needle shroud is a syringe carrier 34 having a forward tubular portion 36 capable of sliding telescopically inside the tubular portion 36 of the needle shroud 24. Extending rearwardly from the tubular portion 36 of the syringe carrier 34 are two arms 38 having opposed inner concave surfaces 40 for slideably receiving the barrel of a syringe and outer concave surfaces 42 for defining with convex inner arcuate surfaces on the arms 30 of the needle shroud 24, cylindrical containment spaces for a pair of shroud springs 44.

A spring guide 46 has two forwardly extending fingers 48 that pass down the centre of a respective spring 44. The spring guide 46 has an over-moulded liner 50 surrounding a circular aperture 52 through which a syringe is passed. The liner serves as a shock absorber for the syringe. The spring guide 46 is a snap fit with the rear end of the syringe carrier 34 as to be described below. The spring guide 46 has a rearwardly extending tubular portion in one side wall of which is a recess 53 for captively receiving a disc magnet 54.

Figure 4:
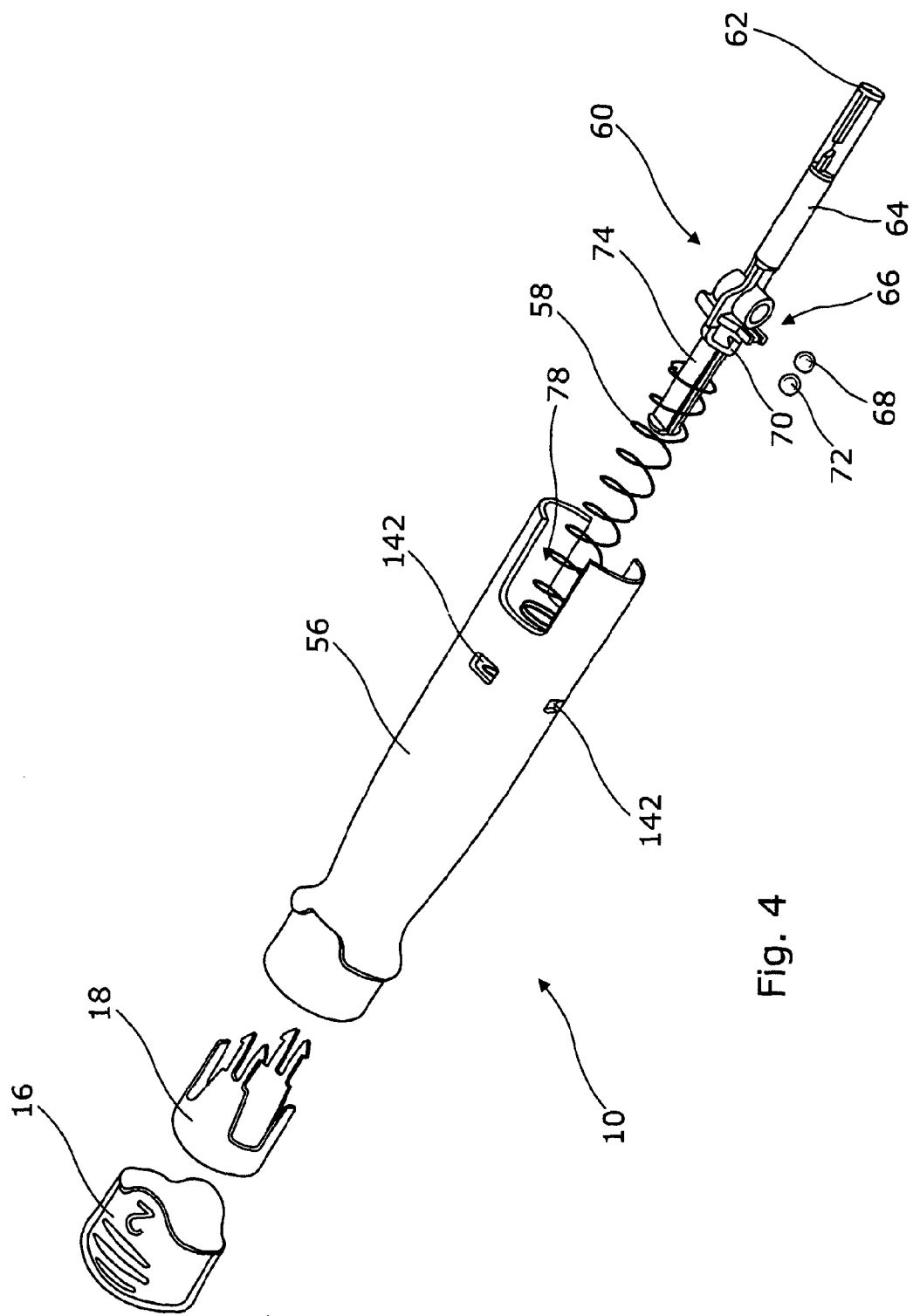
FIG. 4 is an exploded view of the rear assembly.
Figure 9:
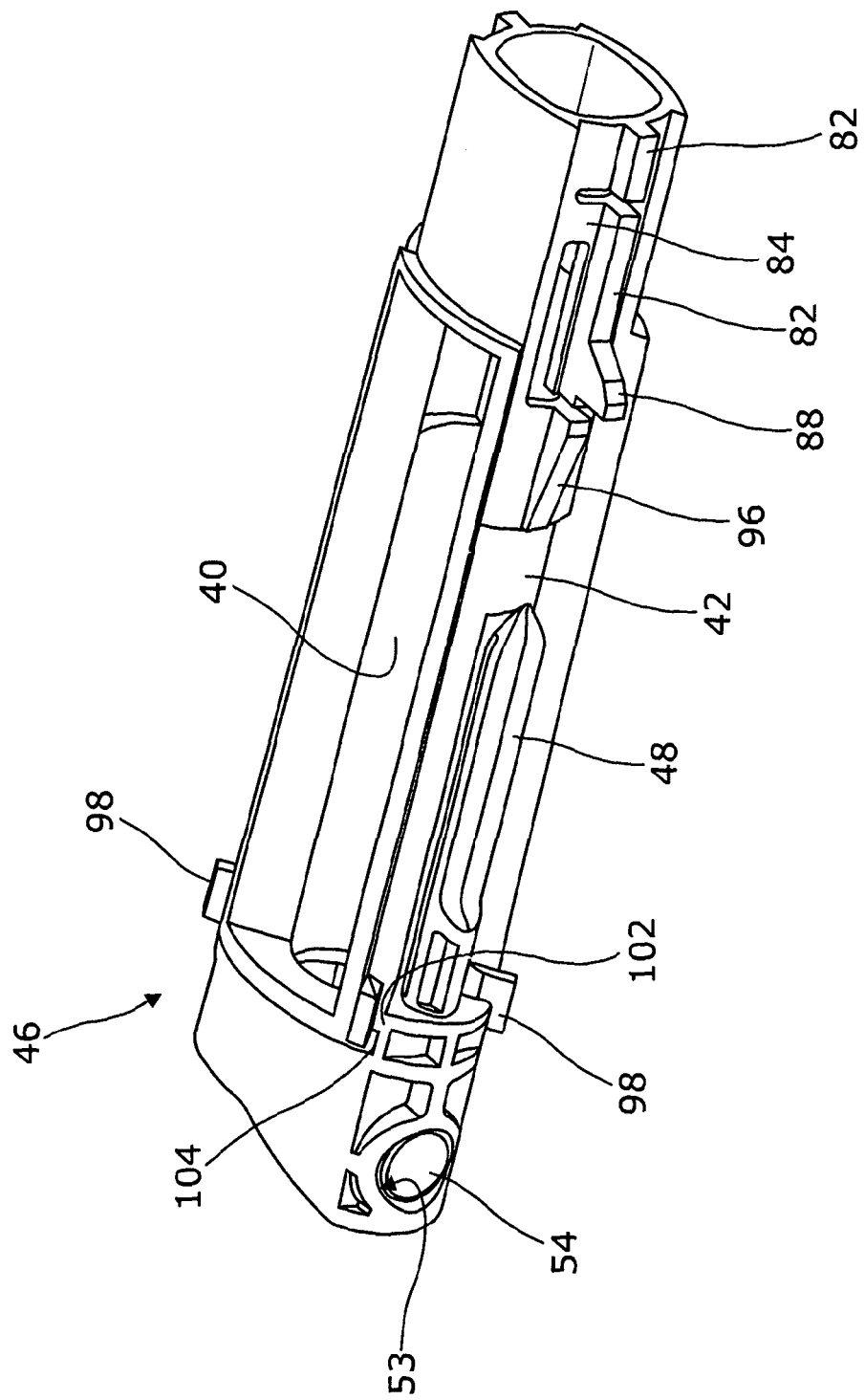
FIG. 9 is a view showing the spring guide and syringe carrier snap-fitted together.

Referring now to FIG. 4, the rear assembly comprises a rear body housing 56 in which is received the main drive spring 58 which acts on the rear end of a plunger 60. The plunger has a forward end 62 for engaging the piston 11 within a syringe and an over-moulded coloured indicator strip 64. To the rear of the indicator strip 64 is a transverse passage 66 in which is mounted for transverse movement a ball magnet 68. To the rear of the passage 66 is a provided a recess 70 which receives a ferro-magnetic keeper ball 72 which is fixedly disposed on the longitudinal axis of the plunger 60. The plunger 60 has two rearwardly extending split arrowhead limbs 74 with barbs 76 on the rear ends which seat around the edge of an annular catchment surface 77 in the inside of the rear body housing 56 (see FIGS. 14 and 15) to latch the plunger in a cocked position, with the main spring 58 compressed.

The autoinjector is of modular construction designed to allow all except two components to be the same for autoinjectors with syringes of three different fill volumes. The shape and the size of the syringe itself is standard; only the fill volume is different. The two components that vary are the rear body housing 10 and the plunger 60. The forward end of the rear body housing 52 contains opposed cut outs or slots 78 which are of variable length according to the fill volume contained in the syringe. The axial length of the slots 78 in the rear body housing 56 is proportional to the fill volume. Also the indicator position moves by the same amount so that it arrives at the same place relative to the body at the end of the plunger stroke. The plunger is also modified according to the fill volume of the syringe to locate the magnet-containing passage 66 so that, at the end of its forward stroke, it reaches the same axial position with respect to the rear body housing 56 for each fill volume. In other words, the plunger 60 and the axial length of the slots 78 are designed so that, for each of the plurality of fill volumes, the user will see prior to use in the viewing window 22 just that length of the syringe containing the dose, with the window being framed at the rear end by the slots 78. After the dose has been delivered, the indicator will be at the same forward position for each fill volume.

Referring now to FIGS. 5 to 9, the assembly of the principal components of the front assembly will be described in more detail. The syringe carrier 34 has twin linear ribs 82 provided to either side of the forward tubular portion 36. The ribs 82 run in respective channels 84 on the inside of the tubular portion 32 of the needle shroud. Immediately behind each rib 82 is a live hinge 85 from which extends back a spring finger 86 with a barb 88 with a rearwardly inclined forward surface. When the syringe carrier is assembled telescopically into the needle shroud 24, the barbs 88 project through slots 90 in the shroud 24 (see FIG. 6) to limit forward movement of the shroud 24 relative to the syringe carrier 34 when the rear ends of the slots 90 contact the barbs 88. Rearward movement of the shroud 24 relative to the syringe cap is limited by a rearward shoulder 92 of the needle shroud tubular portion abutting a forward facing shoulder 94 upstanding from the rear of the tubular portion 36 of the syringe carrier 34. Rearwardly of the barbs 88 on the syringe carrier are two rearwardly facing ramp surfaces 96.

At its rear end, the syringe carrier has four lugs 98 that, when the device is assembled, run in respective slots 100 in the front body portion 20 to limit linear movement of the syringe carrier relative to the front body portion 20. Snap fitted onto the rear of the syringe carrier is the spring guide 46 as shown in FIG. 8. This has snap fit tabs 102 that snap fit around walls 104 on the rear end of the syringe carrier. The tabs also form a platen surface for the shroud springs 44, with the spring guide fingers 48 passing down the centre thereof. The forward ends of the shroud springs are seated on projecting fingers 106 towards the rear of the arms 30 of the needle shroud 24. About two-thirds of the way back from the front of each slot 90 are two barbs 108 with inclined forward surfaces. Behind each slot 90, on a live hinge is a rearward barb 110, again with an inclined forward surface. The barbs 108 and 110 cooperate with respective opposed barbs 112 about a third of the way down the length of the front body housing 20 on the inner walls thereof.

Figure 14B:
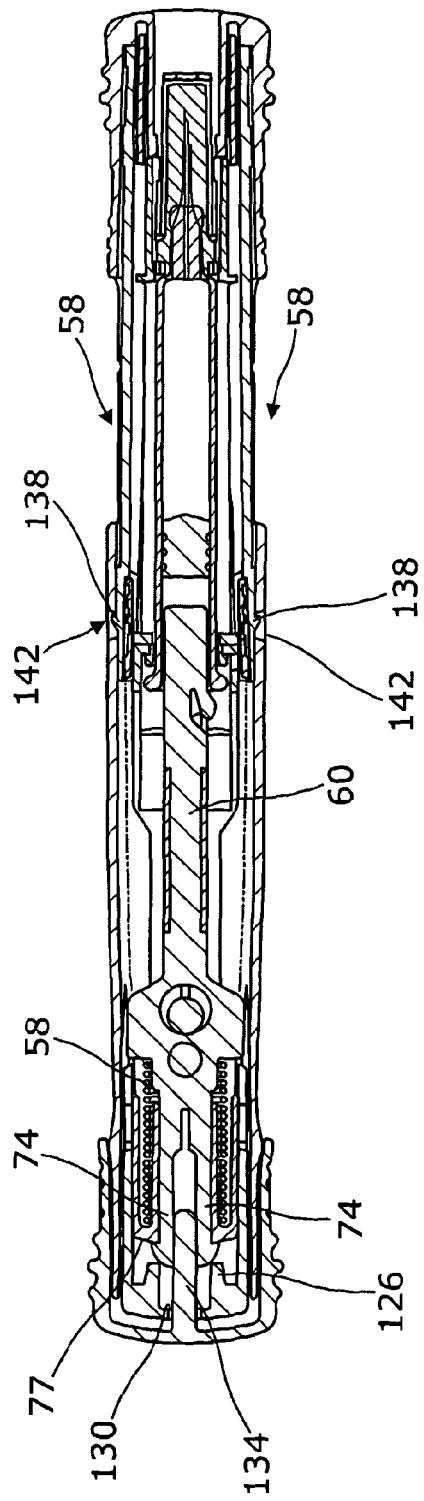

The arrangement of the barbs in the pre-use position can be clearly seen in FIGS. 14 and 15. In the pre-use position, the barbs 108 on the needle shroud cooperate with the barbs 112 on the front body housing to prevent rearward movement of the needle shroud 24. The forward faces of the barbs 88 on the syringe carrier also cooperate with the barbs 112 on the front body housing on the forward housing to prevent forward movement of the syringe carrier 34 prior to and during removal of the front cap 14. Removing the cap removes a bracing on the barbs 88 which initially prevents inward movement of the barbs so that, when fired, the force of the drive spring causes the barbs 88 to cam past the barbs 112 on the front body housing. During operation of the device, when fired, with the needle shroud 24 held against forward movement by its contact with the skin around the injection site, the sub-assembly of the syringe 13 and the syringe carrier 34 is shifted forwardly, relative to the forward housing to a limit position defined by the lugs 98 reaching the forward ends of the slots 100. After the injection is complete, the needle shroud 24 moves forward as the skin contact pressure is removed from the surface 28 as the device is lifted clear of the skin. This allows the needle shroud to move forwardly under the influence of the shroud springs 46 so that the rear barbs 110 move forwardly and snap past the barbs 112 on the front housing 20 to prevent retraction once the needle shroud has extended. The barbs 110 are braced in this position by the underlying ramp surfaces 96 on the syringe carrier 34.

Figure 11:
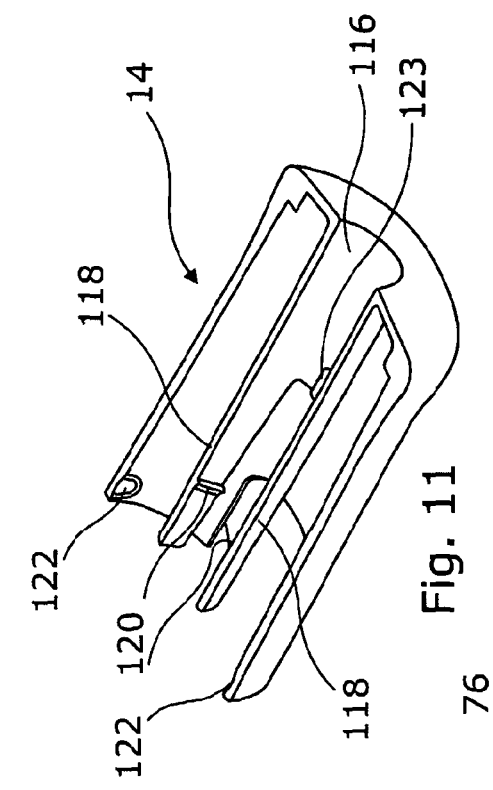
FIG. 11 is a horizontal section view taken through the cap of FIG. 10 on the major axis thereof.
Figure 10:
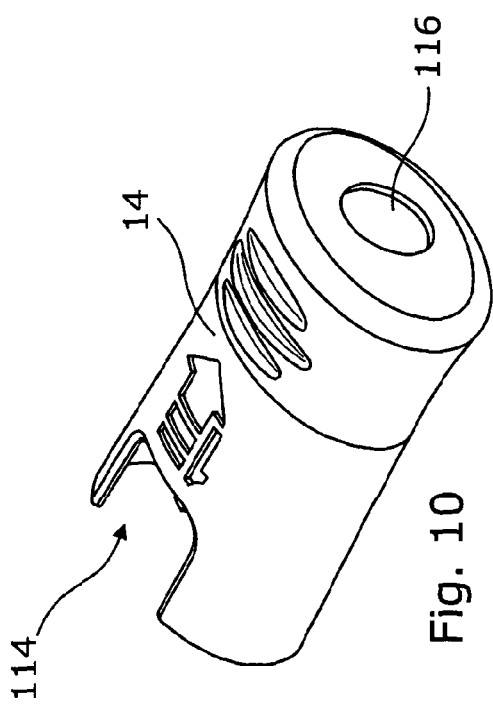
FIG. 10 is an enlarged view of the front cap/needle shield remover.

Referring now to FIGS. 10 and 11, the removable front cap 14 has opposed slots 114 which align with the slots 78 on the rear body housing 56, to frame the window 22 in the front body housing 20 to allow viewing of the dose volume as described above. Referring more particularly to FIG. 11, the cap is elliptical in outer section and has an inner central cylindrical portion 116 extending rearwardly from which extend further two fingers 118 of arcuate cross-section disposed on the major axis of the ellipse. On the inner surface of the fingers, towards the rear ends, are respective inwardly directed barbed ribs 120 with inclined rear surfaces. As seen in FIGS. 14 and 15, the ribs 120 are designed to snap into a gap formed between the forward shoulder on the barrel of the syringe 13 and the rear surface of the rigid needle shield 15 or an aperture therein. When the syringe 13 is loaded into the front assembly 12 (with the cap 14 attached) during manufacture, the rigid needle shroud 15 snaps past the ribs 120 so that they lodge behind the rear edge of the needle shield 15 (or a rear edge of an aperture in the needle shield) as shown. The front cap 14 also has twin shallow scallops 122 which releasably engage pips 124 on the outer surface of the front body housing when the cap is fitted (see FIGS. 14 and 15).

When in the condition as supplied (FIG. 14) the fingers 118 of the cap underlie the spring fingers 86 on the syringe carrier 34 and prevent these from flexing inwardly. In this condition, the fingers 118 thus brace the spring fingers 86 against inward unlatching motion. The forward end of the cylindrical portion 116 of the cap 14 is also provided with inward projections 123 aligned with the minor axis of the ellipse and which prevent forward movement of the rigid needle shield relative to the front cap 14. In this way, when the front cap 14 is withdrawn from the position shown in FIG. 15, the ribs 120 pull the rigid needle shield 15 to ease it off the forward end of the syringe 13. At the same time the presence of the fingers 118 also temporarily locks the syringe carrier 34 (and thus the syringe 13) against forward movement by blocking the fingers 86 against inward movement until the needle shield is off the syringe to prevent the syringe from being pulled forwardly if there is a tight fit between the syringe and the needle shield. When the front cap is free of the device the needle shield 15 is captive in the cap 14, trapped by the ribs 120 and the inward projections 123. Orienting the ribs 120 and the inward projections 123 at 90° means that the open ended cap may be injection-moulded in a simple injection mould with a slide rather than requiring a more complex mould design.

Figure 12:
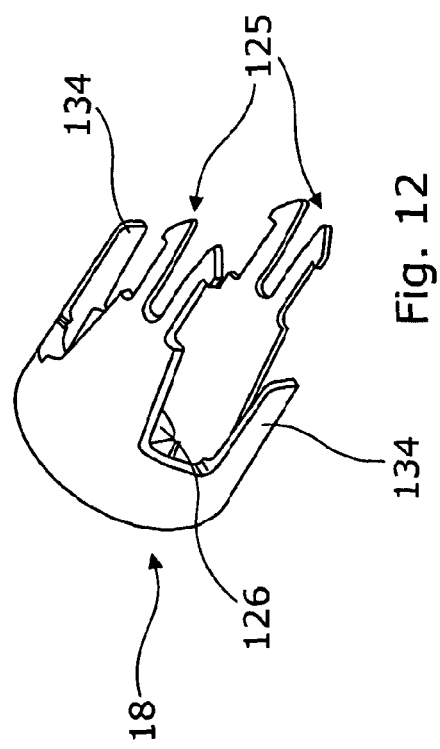
FIG. 12 is an enlarged view of the trigger button.

Referring to FIGS. 4, 12 and 15, the firing button 18 is of elliptical form with two split arrowhead tabs 125 aligned with the minor axis, which seat behind respective ribs on the inner rear surface of the rear housing portion 56 to retain the firing button 18 on the rear of the housing and to limit rearward movement thereof. The inner rear surface of the trigger has a firing boss 126 which is of slightly smaller diameter than the outer diameter of the split arrowheads 74 on the rear of the plunger 60 so that, when the firing button 18 is pressed forwardly from the position shown, the boss squeezes the twin arrowheads 74 together to release the barbs 76 from the catchment surface 77 to free the plunger for forward movement. The firing button 18 has an aperture 130 concentric with the boss 126 through which a safety pin 134 on the rear cap 16 passes to hold the split arrowheads apart. Aligned with the major axis of the ellipse are two forwardly extending flexible biasing strips 134 which cooperate with respective bias camming surfaces 136 in the rear end of the rear housing 56, as shown in FIGS. 14(a) and 15(a) to provide a low friction gliding plastic-to-plastic surface contact. The camming surfaces 136 are shaped to provide a predetermined variation of resistance force with distance. The biasing strips cooperate with the curved rear portion of the camming surfaces to provide a bias force tending to restore the button to its rearmost position as defined by the split arrowhead tabs. It is desirable to provide a tactile resistance to movement and to require a few millimetres of movement before the firing boss 126 releases the plunger, to avoid premature firing. A forward portion of the camming surfaces is of shallower inclination and designed to provide a non-reversible resistance to movement after the device has been fired, thereby to trap or wedge the firing button in its forwardmost position. This gives a further useful visual cue to a user as to whether the device has been fired or not. Of course, if required the camming surface may instead be designed to return the button to its original position after firing.

Figure 13:
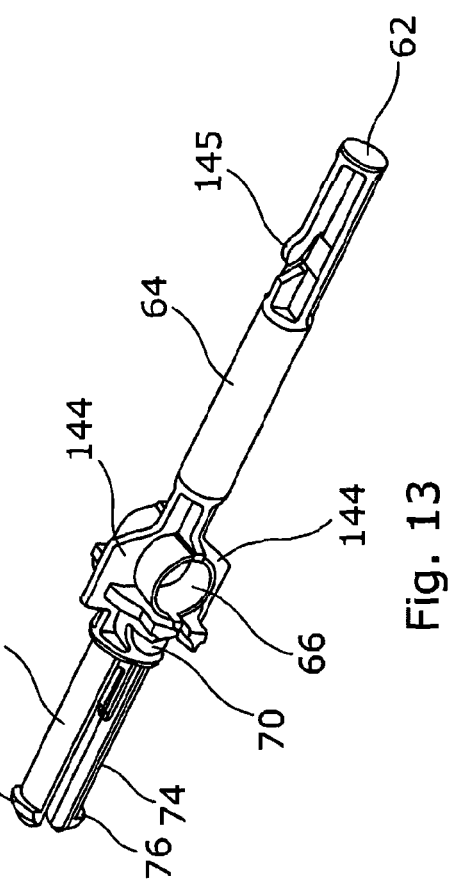
FIG. 13 is an enlarged view of the plunger.
Figure 15B:
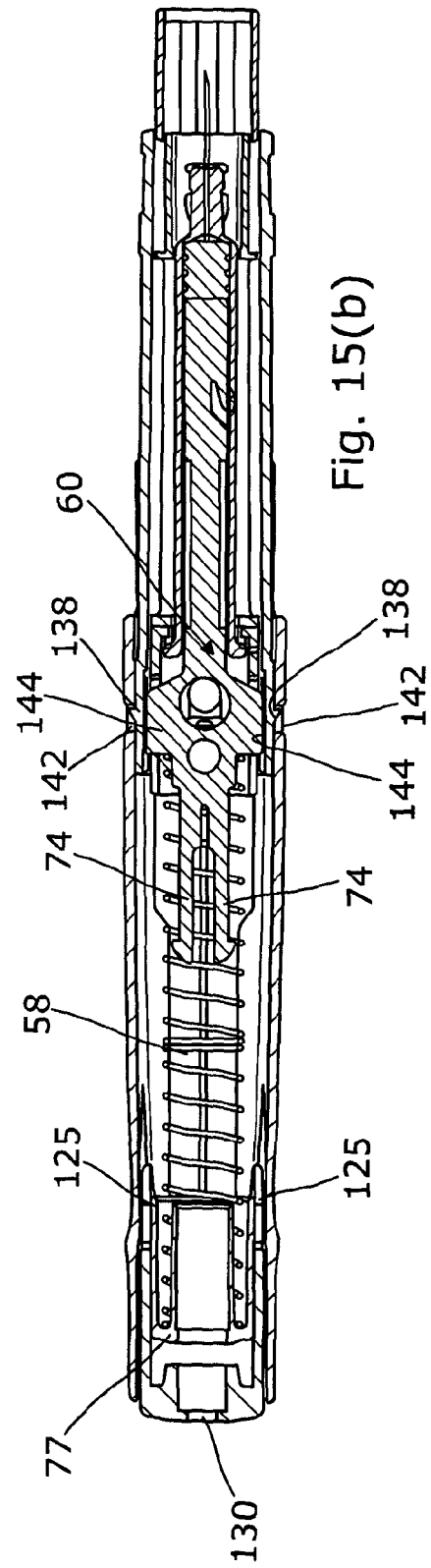

The autoinjector as illustrated includes several safety features to prevent inadvertent firing and to render the device safe after use. It is also highly desirable to resist or prevent disassembly of the device after use. It will be noted from the description and FIG. 2 above that the device is assembled by inserting a syringe into the syringe carrier in the front assembly and then snap-fitting the front and rear assemblies together. The snap fitting is done by means of outwardly facing sprung tabs 138, 140 on the rear of the front body housing 20 which seat simultaneously in respective apertures 142 in the rear body housing 56. One pair of tabs 138 is aligned with the minor axis and one pair 140 with the major axis of the device. It will be appreciated that, given appropriate dexterity and strength, it would be possible to press in all four of the tabs 138, 140 by poking an implement through the recesses 142 from outside and thereby disassemble the device. However, this is prevented in this embodiment by means of two fin formations 144 provided on the plunger 60 as seen in FIGS. 13 and 15(b). The plunger is designed so that, once the device is fired and the plunger is at its post-firing position, the fin formations 144 underlie the tabs 138 on the minor axis of the ellipse, as shown in FIG. 15(b), thereby bracing them against inward deflection and preventing disassembly.

For operation, the user removes the front cap 14 and rear cap 16, thereby arming the device. The device is then offered up to the injection site to press the conical or curved front face of the needle shroud 26 against their skin. When ready, the firing button 18 is pressed, which releases the plunger 60 for forward movement under the action of the main drive spring 58. Initially, due to a sprung engagement finger 145 on the plunger, the plunger and syringe move as one forwardly to extend the needle to penetrate the flesh, with this movement continuing until the lugs 98 on the syringe carrier reach the forward end of the slots 100 on the front body housing, thereby inserting the syringe needle to the required depth. Upon arresting movement of the syringe, the sprung engagement finger 145 flexes inwardly into the bore of the syringe and the plunger continues to move, driving the piston 11 down the syringe body to expel a dose. Alternatively, in other designs of the device, the spring engagement finger may yield so that the plunger starts to move into the syringe before forward movement of the latter is arrested. In either design, when the plunger reaches its forwardmost position, the ball magnet 68 which up till now has been held in the passage 66 on the centre line of the plunger by magnetic attraction to the keeper ball 72 is attracted by the greater force provided by the disc magnet 54 held in the recess of the spring guide, accelerating towards it and impacting the magnet and/or spring guide to produce a loud audible click to indicate to the user that the injection is complete.

The user then removes the device from their skin and the release of pressure on the front end of the needle shroud 24 means that it can now extend forwardly under the influence of the twin shroud springs 44 to move forwardly to shield the needle. As it nears its forwardmost position, the barbs 110 snap past the barbs 112 on the inside of the front housing 20 thereby to prevent retraction of the needle shroud.

Figure 17:
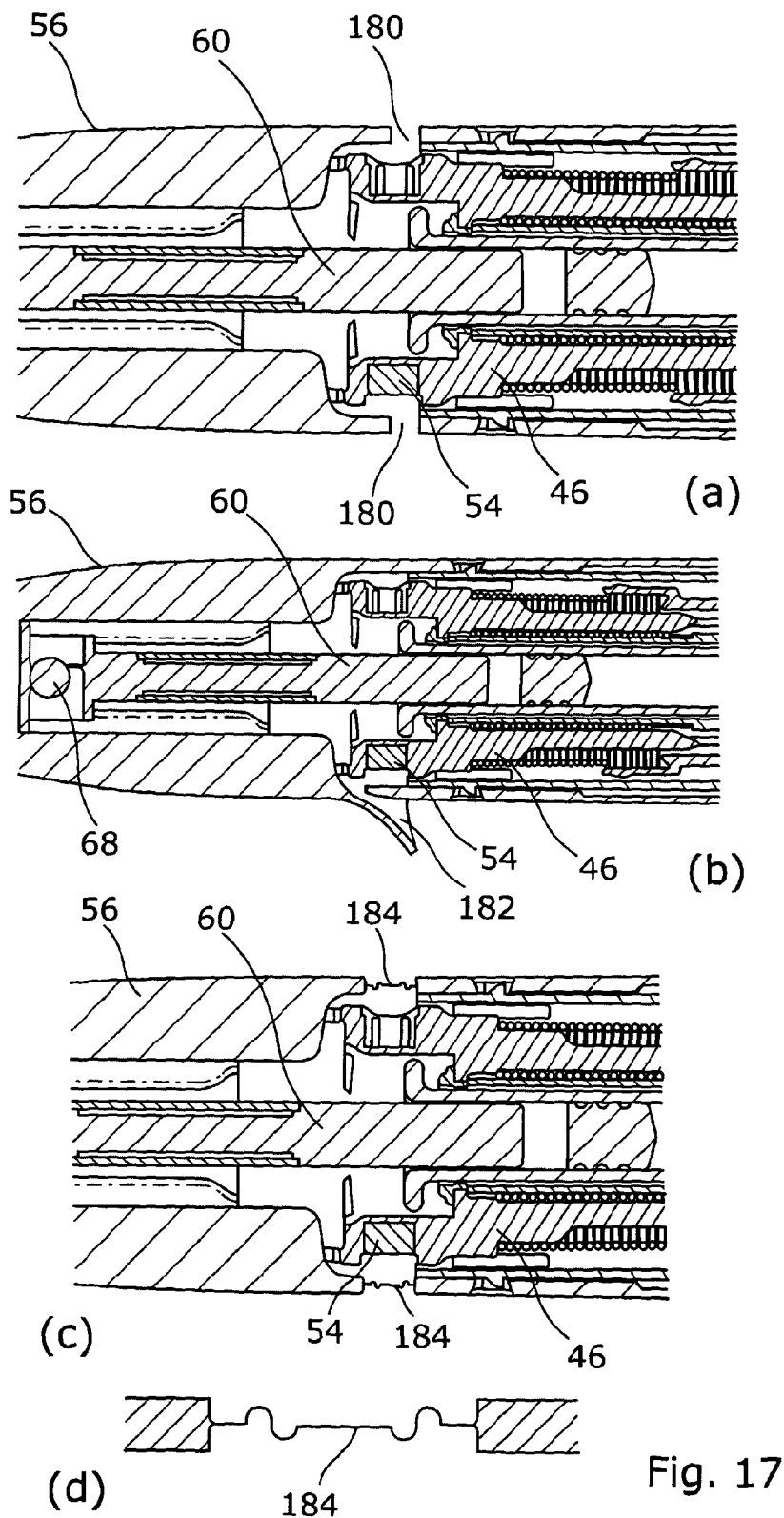

Referring now to FIGS. 17(*a*) to (*d*) there were shown various ways in which the audible sound signal emitted when the ball magnet 68 on the plunger 60 impacts the disc magnet 54 on the spring housing 56 may be enhanced for those of poor hearing. In the example of FIG. 17(*a*) the housing 56 is cut away to provide an aperture 180 to allow transmission of the audible signal to the user. The shape and diameter or throat of the passage may be modified to provide a sound box or a sound-enhancing effect. FIG. 17(*b*) shows a horn type arrangement 182 which is designed to maximise the audible signal to the user. Likewise, in FIGS. 17(*c*) and (*d*), a drum 184 surface is provided which is designed to provide good acoustic coupling of the signal emitted by the impact of the ball magnet and disc magnet to the user. Still further the audible sound may be enhanced by suitable modification of the interface between the disc magnet and the component by which it is supported.

Figure 18:
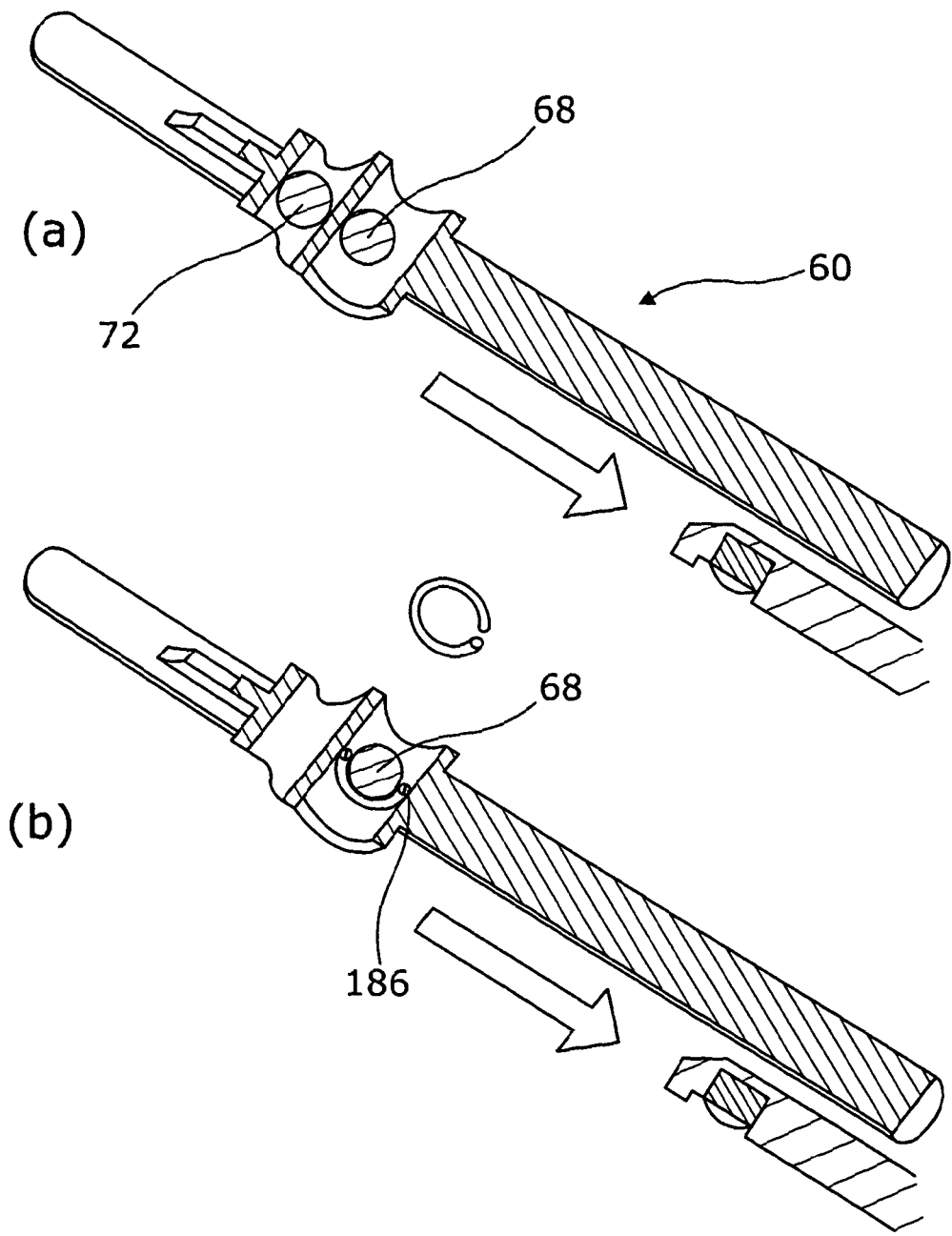

Referring to FIGS. 18(*a*) and 9(*b*), FIG. 18(*a*) shows the arrangement as set out in the above description whereby the keeper is a ferromagnetic ball 72 statically housed in the plunger 60 on the longitudinal axis thereof. FIG. 18(*b*) shows an alternative arrangement where the keeper 186 is in the form of a ring of ferro-magnetic material of diameter larger than the movable magnetic ball 68, but providing a 360° encompassment. Either type of arrangement is suitable for use in the wide range of devices in accordance with this invention.

In the above embodiments, the ball magnet 68 and disc magnet 56 are magnets whereas the keepers are non-magnetised ferro-magnetic material. It will be appreciated that other arrangements may be used which rely on the magnet attraction between either two magnets, or a magnet and a ferro-magnetic material.

The invention claimed is:

1. An autoinjector comprising:
   a body (10, 12),
   a syringe (13) or cartridge disposed within said body, and
   an elongate plunger (60) movable longitudinally during operation between a first position and a second position to effect an injection,
   the plunger having a center, and a longitudinal axis extending through the center of the plunger and parallel to a longitudinal direction of the autoinjector,
   the plunger including a transverse passage (66) containing a moveable magnetic element (68) of a magnetic pair,
   the body including another magnetic element (54) at a position such that, on said plunger reaching and/or nearing the second position, the magnetic attraction therebetween causes a sound-emitting impact,
   the plunger (60) including a magnetic keeper element (72) fixedly mounted adjacent said transverse passage and adapted to hold the movable magnetic element (68) against movement until attraction by the other magnetic pair element (54), wherein said keeper element (72) is disposed on said longitudinal axis of the plunger.

2. An autoinjector according to claim 1, wherein the moveable magnetic element (68) comprises a magnetic ball.

3. An autoinjector according to claim 1, wherein the magnetic element (54) associated with said body comprises a disc magnet.

4. An autoinjector according to claim 1, wherein said keeper (72) element comprises a keeper element of ferromagnetic material.

5. An autoinjector according to claim 2, wherein the magnetic element (54) associated with said body comprises a disc magnet.

6. An autoinjector according to claim 2, wherein said keeper (72) element comprises a keeper element of ferromagnetic material.

7. An autoinjector according to claim 6, wherein said keeper element is a ball (72) element.

8. An autoinjector according to claim 3, wherein said keeper (72) element comprises a keeper element of ferromagnetic material.

9. An autoinjector according to claim 8, wherein said keeper element is a ring or part ring-shaped generally coaxial with said transverse passage.

10. An autoinjector comprising:
    a body (10, 12),
    a syringe (13) or cartridge disposed within said body, and
    an elongate plunger (60) movable longitudinally during operation between a first position and a second position to effect an injection,
    the plunger having a center, and a longitudinal axis extending through the center of the plunger and parallel to a longitudinal direction of the autoinjector,
    the plunger including a transverse passage (66) containing a moveable magnetic element (68) of a magnetic pair,
    the body including another magnetic element (54) at a position such that, on said plunger reaching and/or nearing the second position, the magnetic attraction therebetween causes a sound-emitting impact,
    the plunger (60) including a magnetic keeper element (72) fixedly mounted adjacent said transverse passage and adapted to hold the movable magnetic element (68) against movement until attraction by the other magnetic pair element (54), wherein said keeper element (72) is disposed on said longitudinal axis of the plunger,
    wherein said keeper element is a ball element (72) of ferro-magnetic material fixedly disposed against a first side of a wall of a recess (70) of the elongate plunger (60), wherein with the elongate plunger (60) in the first position, said movable magnetic element (68) is held against a second side of the wall of the recess (70) by magnetic attraction with the ball element (72) and in said second position, said movable magnetic element (68) is spaced apart from said second side of the wall of the recess (70).

11. An autoinjector comprising:
    a body (10, 12),
    a syringe (13) or cartridge disposed within said body, and
    an elongate plunger (60) movable longitudinally during operation between a first position and a second position to effect an injection, the plunger having a center, and a longitudinal axis extending through the center of the plunger and parallel to a longitudinal direction of the autoinjector, the plunger including a transverse passage (66) containing a moveable magnetic element (68) of a magnetic pair, the body including another magnetic element (54) at a position such that, on said plunger reaching and/or nearing the second position, the magnetic attraction therebetween causes a sound-emitting impact, the plunger (60) including a magnetic keeper element (72) fixedly mounted adjacent said transverse passage and adapted to hold the movable magnetic element (68) against movement until attraction by the other magnetic pair element (54), wherein said keeper element (72) is disposed on said longitudinal axis of the plunger, wherein said keeper element is a ring or part ring-shaped element (186) of ferro-magnetic material having a diameter generally coaxial with said transverse passage, the diameter of said ring or part ring-shaped element (186) being greater than a diameter of said movable magnetic element (68), and wherein with the elongate plunger (60) in the first position, said movable magnetic element (68) is held in and is encompassed by said ring or part ring-shaped element (186) by magnetic attraction with said ring or part ring-shaped element (186), and in said second position, said movable magnetic element (68) is spaced apart from said ring or part ring-shaped element (186).

\* \* \* \* \*